United States Patent [19]
Miyai et al.

[11] 4,158,641
[45] Jun. 19, 1979

[54] FLUORESCENT DENTAL PORCELAIN

[75] Inventors: Kozo Miyai, Hirakata; Narishige Suzuki, Kyoto; Takaya Kawakami, Kyoto; Ikuo Kuze, Kyoto, all of Japan

[73] Assignee: Shofu Dental Manufacturing Co., Ltd., Kyoto, Japan

[21] Appl. No.: 835,659

[22] Filed: Sep. 22, 1977

[30] Foreign Application Priority Data

Oct. 26, 1976 [JP] Japan .................................. 51-128974

[51] Int. Cl.$^2$ ........................ C09K 11/46; A61C 13/00
[52] U.S. Cl. .................................. 252/301.4 F; 32/8; 106/35; 106/45; 252/301.4 R
[58] Field of Search .................. 252/301.4 R, 301.4 F; 106/35, 45; 32/8

[56] References Cited

U.S. PATENT DOCUMENTS

| 2,377,382 | 6/1945 | Slack | 32/8 X |
| 2,895,050 | 7/1959 | Lee et al. | 252/301.4 F X |

OTHER PUBLICATIONS

Isaacs, "J. Electrochem. Soc.," vol. 118, No. 6, (1971), pp. 1009–1011.
Laud et al., "J. Electrochem. Soc.," vol 118, No. 6, (1971), pp. 918–923.
Verstegen, "J. Electrochem. Soc., 38 vol. 121, No. 12, (1974), pp. 1623–1627.

*Primary Examiner*—Jack Cooper
*Attorney, Agent, or Firm*—Eugene E. Geoffrey, Jr.

[57] ABSTRACT

A porcelain dental composition for artificial teeth which includes an aluminum silicate, alkali or alkaline earth aluminosilicate or an alkali or alkaline earth aluminate fluorescent material and an activator including europium.

4 Claims, No Drawings

FLUORESCENT DENTAL PORCELAIN

This invention relates to an improved porcelain material used for manufacturing artificial porcelain teeth which can exhibit fluorescence by excitation with near ultra-violet ray and show a color tone similar to that of natural teeth.

The natural teeth exhibit fluorescence by excitation with near ultra-violet ray and this fluorescence contributes to the white appearance of the teeth. When artificial teeth having no fluorescent property are arranged with natural teeth, they may appear extraordinarily dark as compared with the natural teeth under the same condition of illumination. Efforts have been made many years to provide a fluorescent property for artificial teeth but such efforts have not succeeded. Artificial teeth can be classified into synthetic resin teeth and porcelain teeth. While it is relatively easy to give a fluorescent property to the former since no high processing temperature is required, it has been believed that the latter is more closely allied to the natural teeth in view of refractive index, hardness, anti-abrasive property and feeling in use.

On the other hand, in case of the artificial porcelain teeth which are fired at about 1000° C. during the manufacturing process, fluorescent substances for near ultra-violet ray excitation, which belong to zinc sulfide family, magnesium germanate family and organic family, for example, are decomposed or diffused into the porcelain material by this firing temperature and hardly conserve the fluorescent property. Although there are some other fluorescent substances which can withstand this firing termperature, they can not produce a color tone which is closely allied to the natural teeth due to their reddish tint of fluorescence. Accordingly, only the substances of the uranium family have been adopted as they generally withstand the firing temperature and exhibit fluorenscence closely allied to the natural teeth. As uranium is a radioactive substance, however, it is undesirable for the human body regardless of its minute dose. Moreover, the porcelain teeth containing uranium exhibit a natural color with darkish tint due to the blackish appearance of uranium oxide.

Accordingly, an object of this invention is to provide a fluorescent dental porcelain composition which is proof against its firing temperature in conserving its fluorescent property and has no radioactivity but exhibits fluorescent and natural colors having tones closely allied to the natural teeth.

The fluorescent dental porcelain composition according to this invention comprises a porcelain material for artificial teeth and a fluorescent substance dispersed therein. The fluorescent substance comprises a basic material including aluminate or aluminosilicate of alkali or alkali-earth metal or aluminium silicate and an activating agent or activator including europium.

The above porcelain material for artificial teeth is a conventional one which includes, as a main material, feldspar, leucite, alumina or syenite. The porcelain material of this kind includes some or all of $SiO_2$, $Al_2O_3$, $K_2O$, $B_2O_3$, $Na_2O$, BaO and MgO, consists of a relatively large quantity of glassy texture and relatively small quantity of crystalline texture, exhibits softening temperature of 600° to 800° C. and can be vitrified when fired at 900° to 1300° C.

The alkali metal may be sodium or potassium and the alkali-earth metal may be magnesium, calcium, barium or strontium. Combinations of some of these metals are also usable. The content of these metals may be determined arbitrarily, but an insufficient luminosity is obtainable if the molar content of the metals exceeds four times of the molar content of alumina included in the aluminate or aluminosilicate radical.

It is generally believed that the fluorescent substances containing europium activator exhibit red fluorescence in case of trivalent europium but blue fluorescence in case of divalent europium. The porcelain composition according to this invention, which contains only europium as the activator, exhibits blue-white or violet-white fluorescence after it is fired. Therefore, it is presumed that the fluorescent substance is not decomposed so much by firing and most of europium is left as it is divalent. Even if a part of europium is transformed into trivalent europium, it tends to extend its wavelength distribution to bring the fluorescent color from blue to white, thereby contributing to production of color which is closely allied to the natural teeth. A part of europium may be substituted by another element or another element may be added to the europium activator, whereby the wavelength distribution is extended to enable production of fluorescent colors which are more closely allied to the natural teeth.

As the amount of addition of the fluorescent substance to the porcelain material, one percent by weight or less is enough for the purpose. Accordingly, the content of europium with respect to the porcelain material is 0.01 percent by weight or less. The content of europium, calculated as $Eu_2O_3$, is not more than four percent by weight of the fluorescent substance present in said porcelain material. This results in low cost of the porcelain composition of this invention.

Furthermore, the natural body color of the fluorescent substance used in this invention is white and it scarcely makes the porcelain composition muddy or cloudy to reduce its clarity or transparency. Therefore, it is easy to produce porcelain compositions having natural colors which are closely allied to the natural teeth.

Now, the features and advantages of this invention will be described with reference to some embodiments.

EXAMPLE 1

Barium carbonate, magnesium hydroxide and aluminium hydroxide were mixed at a ratio which was adequate for producing $(BaO.2MgO)7Al_2O_3$ and one percent by weight of europium oxide $Eu_2O_3$ was added thereto. The mixture was ground in a mortar, press-shaped, fired at 900° C. in air and then pulverized. The pulverized particles were press-shaped again, fired at 1320° C. for two hours in a nitrogen atmosphere containing ten percent by volume of hydrogen and then pulverized to obtain powdered fluorescent substance. This fluorescent substance was added in a powdered porcelain material of leucite family (containing K, Si, Al and B as the main ingredients) by one percent by weight with respect to the latter and mixed up to obtain a fluorescent dental ceramic composition according to this invention.

This porcelain compositiom was kneaded with water, built up on a metallic tooth crown, heated up to about 960° C. in a vacuum furnace at a pressure of about 60 mmHg and then fired at 980° C. in the same furnace in air introduced therein.

A porcelain tooth with metallic crown prepared as above exhibited fluorescence with greenish blue-white color when illuminated with ultra-violet ray of about 3650 Å wavelength. Although the fluorescent color of the fluorescent substance obtained as aforementioned is blue-white, the wavelength of the fluorescence was shifted somewhat to become longer by the firing within the porcelain material.

EXAMPLE 2

In similar fashion to Example 1, a powdered fluorescent substance consisting of $(CaO.2MgO).7Al_2O_3$ containing one percent by weight of $Eu_2O_3$ was prepared. This powdered fluorescent substance was added in the same porcelain material as Example 1 by one percent by weight with respect to the latter to obtain another fluorescent dental porcelain composition according to this invention.

A porcelain tooth prepared with this porcelain composition in similar fashion to Example 1 exhibited fluorescence with blue-white color by excitation of ultra-violet ray of 3650 Å.

EXAMPLES 3 to 10

Eight kinds of aluminosilicate fluorescent substances activated by europium were prepared in the same fashion. As shown in Table 1, these fluorescent substances differ from each other in $SiO_2$ content and/or alkali or alkali-earth metal content in the aluminosilicate. For example, the $SiO_2$ content is lowest in Example 3, while the alkali-earth metal content is relatively low in Example 8 but is very high in Examples 9 and 10. $Eu_2O_3$ was added in the basic material of the each fluorescent substance by the amount as shown in the table in percent by weight with respect to the basic material. Each fluorescent substance was added in the same porcelain material as used in the foregoing examples by the amount as shown in the table in percent by weight with respect to the latter, to obtain eight kinds of fluorescent dental porcelain compositions according to this invention.

Test porcelain teeth were prepared in the same fashion as in the foregoing examples and their fluorescent colors were observed under 3650 Å ultra-violet ray illumination as shown in the table.

TABLE 1

| Example No. | Basic material of fluorescent substance | $Eu_2O_3$ (%) | Fluores. subst. (%) | Color of fluorescence |
|---|---|---|---|---|
| 3 | $(BaO . 2MgO) . 5Al_2O_3 . SiO_2$ | 1 | 1 | violet-white |
| 4 | $(BaO . 2MgO) . 7Al_2O_3 . 8SiO_2$ | 1 | 0.1 | blue |
| 5 | $(SrO . 2MgO) . 7Al_2O_3 . 8SiO_2$ | 1 | 0.1 | blue-violet |
| 6 | $(CaO . 2MgO) . 7Al_2O_3 . 8SiO_2$ | 1 | 1 | blue |
| 7 | $(\frac{1}{2}Na_2O . MgO) . 7Al_2O_3 . 8SiO_2$ | 1 | 1 | blue |
| 8 | $\frac{1}{3}(BaO . 2MgO) . 7Al_2O_3 . 8SiO_2$ | 2 | 1 | blue-white |
| 9 | $8(BaO . 2MgO) . 7Al_2O_3 . 8SiO_2$ | 2 | 1 | milky white-blue |
| 10 | $6(SrO . 2MgO) . 7Al_2O_3 . 3SiO_2$ | 2 | 1 | blue-white |

EXAMPLE 11

Two kinds of fluorescent substances were prepared in the foregoing fashion with different basic materials and different activator contents, and added in the same porcelain material by different amounts, respectively, as shown in Table 2, to obtain a further fluorescent dental porcelain composition according to this invention. Fluorescence was observed under the same condition as the foregoing examples, as shown in the table.

TABLE 2

| Example No. | Basic material of fluorescent substance | $Eu_2O_3$ (%) | Fluores. subst. (%) | Color of fluorescence |
|---|---|---|---|---|
| 11 | $(SrO . 2MgO) . 7Al_2O_3 . 8SiO_2$ | 1 | 0.35 | blue-white |
|  | $\frac{3}{8}(SrO . 2MgO) . 7Al_2O_3 . 8SiO_2$ | 4 | 0.15 |  |

EXAMPLES 12 and 13

In these examples, $(BaO.2MgO).7Al_2O_3.8SiO_2$ was used as the basic material of the both fluorescent substances. Although both fluorescent substances were activated with europium as in the foregoing examples, cerium and ytterbium were added respectively as auxiliary activators. Cerium and ytterbium were added in the forms of $CeO_2$ and $Yb_2O_3$, respectively, by the amount as shown in Table 3 in percent by weight with respect to the basic material. The fluorescent substances were added to the same porcelain material as aforementioned by one percent each by weight to obtain two kinds of fluorescent dental porcelain compositions of this invention.

Test teeth were prepared in the same fashion and their fluorescences were observed under the same condition as the above examples, as listed in the table.

TABLE 3

| Example No. | $Eu_2O_3$ (%) | $CeO_2$ (%) | $Yb_2O_3$ (%) | Fluores. substance (%) | Color of fluorescence |
|---|---|---|---|---|---|
| 12 | 1 | 1 | — | 1 | blue-white |
| 13 | 2 | — | 1 | 1 | blue |

EXAMPLE 14

In this example, two kinds of fluorescent substances were added in the same porcelain material to obtain a fluorescent porcelain composition according to this invention. $(BaO.2MgO).7Al_2O_3.8SiO_2$ was used as the basic material of both fluorescent substances, while one percent by weight of $Eu_2O_3$ was added in the first fluorescent substance and one percent by weight of $Yb_2O_3$ was added in the second fluorescent substance, as the respective activators. 0.05% by weight of the first fluorescent substance and 0.5% by weight of the second fluorescent substance were added in the same powdered porcelain material to obtain a fluorescent porcelain composition of this invention. The color of fluorescence observed under the same condition as above was milky white-blue.

Aluminosilicates of alkali-earth metals activated with such other elements as ytterbium are not as bright or fluorescent by themselves, in general. However, when they are intermixed in the powdered powdered porcelain material together with the fluorescent substance activated with europium as in the case of this example, the brightness of fluorescence is raised above the case of using the fluorescent substance activated with europium only and moreover, the color of fluorescence can be modified.

EXAMPLE 15

As in Example 11, two kinds of fluorescent substances activated with europium were added in the same powdered porcelain material to obtain a fluorescent porcelain composition of the invention. In this example, however, one fluorescent substance included, as the basic material, yttrium vanadate which is completely different from the basic material according to this invention, though the other fluorescent substance included an aluminosilicate of alkali-earth metal. Yttrium vanadate activated with europium is excited by ultra-violet ray of 3650 Å and exhibits red fluorescence. Accordingly, this fluorescent substance itself is unsuitable for use in artificial teeth. However, it is useful for adjustment of the color of fluorescence of porcelain teeth when it is used together with the fluorescent substance of this invention. The composition and fluorescence were as listed in Table 4.

TABLE 4

| Example No. | Basic material of fluorescent substance | $Eu_2O_3$ (%) | Fluores. subst (%) | Color of fluorescence |
|---|---|---|---|---|
| 15 | $YVO_4$ | 1 | 0.05 | white |
| | ½(BaO . 2MgO) . $7Al_2O_3$ . $8SiO_2$ | 2 | 0.01 | |

EXAMPLE 16

In this example, aluminium silicate which was completely free from alkali or alkali-earth metals was used as the basic material of the fluorescent substance. Two percent by weight of $Eu_2O_3$ was added in $3Al_2O_3.2SiO_2$ to obtain a fluorescent substance in the same fashion as above and 0.5% by weight of this fluorescent substance was added in the same powdered porcelain material to obtain a fluorescent porcelain composition of this invention. The color of fluorescence observed under the same condition as above was blue-violet-white.

EXAMPLE 17

$3BaO.7Al_2O_3.8SiO_2$ was used as the basic material of fluorescent substance and one percent by weight of $Eu_2O_3$ was added therein as the activator. In the same fashion as Example 1, a fluorescent substance was prepared and, then, added in a powdered porcelain material of feldspar family (containing K, Si, Al and B as main ingredients) by one percent by weight of the latter. The composition was added with three percent by weight of polyvinyl alcohol and mixed up, then kneaded with water and formed into a porcelain tooth without use of metallic tooth crown. The tooth was heated up to 1100° C. in a vacuum furnace at about 60 mmHg and then fired at 1280° C. in air introduced therein. This porcelain tooth exhibited blue-white fluorescence when excited by ultra-violet ray of 3650 Å.

Although, in the abovementioned examples, europium and other activating elements were added in the basic material in the form of oxide, it should be easily understood by those skilled in the art that similar results would be obtained when they were added in the other forms such as hydroxide, carbonate and sulfide if their contents were equivalent to the oxides of the foregoing examples.

As clarified by these examples, according to the fluorescent dental porcelain composition of this invention, it is possible to conserve high luminosity of fluorescence regardless of high firing temperature such as about 1000° C. or above and, moreover, to render its color of fluorescence to be closely allied to that of the natural teeth. Furthermore, as the basic material of the fluorescent substance is white and does not badly affect the clarity or transparency of the fired porcelain, it is possible to obtain artificial teeth having both natural and fluorescent colors being allied to the natural teeth. In addition, these artificial teeth are safe to human health as they have no radioactivity.

What is claimed is:

1. A fluorescent dental composition, comprising a porcelain material for artificial teeth, that includes as a main material, feldspar, leucite, alumina or syenite; said porcelain material exhibiting a softening temperature of 600° C. to 800° C. and undergoes vitrification at a temperature of 900° C. to 1300° C; a fluorescent substance therein, said fluorescent substance consisting essentially of an aluminum silicate, alkali metal aluminosilicate, alkaline earth metal aluminosilicate, alkali metal aluminate, alkaline earth metal aluminate, or mixtures thereof wherein said alkali metal is sodium or potassium and said alkaline earth metal is magnesium, calcium, barium or strontium; and an activator therefor selected from the group consisting of europium, and europium and at least one of cerium or ytterbium as an auxiliary activator; and wherein said fluorescent substance is present in said dental composition in a concentration of not more than one percent by weight of said porcelain material;

said europium, calculated as $Eu_2O_3$, is present in an amount of not more than four percent by weight of said fluorescent substance;

the molar content of alkali or alkaline earth metal present calculated as the oxide thereof does not exceed four times the molar content of alumina present in said fluorescent substance; and wherein said fluorescent dental composition exhibits a fluorescence within the range of violet white to milky white blue when excited by ultra-violet radiation of about 3650 Å wavelength.

2. A fluorescent dental composition as claimed in claim 1, wherein said auxiliary activator is cerium.

3. A fluorescent dental composition as claimed in claim 1, wherein said auxiliary activator is ytterbium.

4. A fluorescent dental composition, comprising a porcelain material for artificial teeth that includes leucite as a main material; as a fluorescent substance therein europium activated ½(BaO,2MgO).$7Al_2O_3$.$8SiO_2$ and a europium-activated yttrium vanadate that exhibits red fluorescence when excited by ultra-violet radiation of 3650 Å, said fluorescent dental composition exhibiting a white fluorescence when excited by an ultra-violet radiation of about 3650 Å wavelength.

* * * * *